United States Patent [19]
Berger et al.

[11] Patent Number: 5,687,211
[45] Date of Patent: Nov. 11, 1997

[54] BONE DENSITOMETRY SCANNING SYSTEM AND METHOD FOR SELECTING SCAN PARAMETRIC VALUES USING X-RAY THICKNESS MEASUREMENT

[75] Inventors: Noah Berger, Waltham; Joel B. Weinstein, Framingham; Dao-Yi Zhu, Lynn, all of Mass.

[73] Assignee: Hologic, Inc., Waltham, Mass.

[21] Appl. No.: 525,909

[22] Filed: Sep. 8, 1995

Related U.S. Application Data

[63] Continuation-in-part of Ser. No. 345,069, Nov. 25, 1994, which is a continuation-in-part of Ser. No. 156,287, Nov. 22, 1993, Pat. No. 5,432,834.

[51] Int. Cl.$^6$ .................................................. G21K 5/10
[52] U.S. Cl. ............................................. 378/196; 378/146
[58] Field of Search ................................. 378/196, 197, 378/146, 95, 53, 54, 55

[56] References Cited

U.S. PATENT DOCUMENTS

| | | | |
|---|---|---|---|
| 3,715,588 | 2/1973 | Rose | 378/53 |
| 3,803,417 | 4/1974 | Kok . | |
| 3,944,830 | 3/1976 | Dissing . | |
| 3,988,585 | 10/1976 | O'Neill et al. . | |
| 4,107,531 | 8/1978 | Garratt et al. | 378/16 |
| 4,144,457 | 3/1979 | Albert . | |

(List continued on next page.)

FOREIGN PATENT DOCUMENTS

| | | | |
|---|---|---|---|
| 0432730 | 6/1991 | European Pat. Off. . | |
| 0461028 | 12/1991 | European Pat. Off. . | |
| 2238706 | 2/1974 | Germany | 378/196 |
| WO8607531 | 12/1986 | WIPO . | |
| WO9421174 | 9/1994 | WIPO . | |

OTHER PUBLICATIONS

Performance Comparison: Multiple vs. Single Beam X-ray Bone Densitometry, Hologic, Inc. Sep. 1982.

Lunar DP3 User's Manual, Dual–Photon Scanner, pp. 4, 8, 10 and 22 (undated).

Nucletron, A New Dimension In Dual–Photon Absorptiometry, Brochure, Novo Diagnostic (undated).

Lunar, A Quantum Leap in Bone Densitometry, Expert, The World's First Imaging Densitometer (undated but beleived to have been published before Nov. 22, 1992).

Lunar News, Dec. 1992, "Lunar Introduces EXPERT, the World's First Imaging Densitometer."

Product Information, EXPERT, Today's Breakthrough—Tomorrow's Standard (undated, but believed to have been published before Nov. 22, 1993).

Hanson, L., et al., "Preliminary Evaluation of a New Imaging Bone Densitometer," Presented at the Fourth International Symposium on Osteoporosis, 27–31 Mar., 1993, Hong Kong.

(List continued on next page.)

*Primary Examiner*—David P. Porta
*Attorney, Agent, or Firm*—Cooper & Dunham LLP

[57] ABSTRACT

Best scan parametric values of a x-ray bone densitometry scanning system for a particular patient is selected according to a thickness of the patient. An operator initially selects scan parametric values of a fast mode scan which is the recommended default, and then commences the fast mode scan. At the initial portion of the scan, the x-ray thickness of the patient is measured. If the measured x-ray thickness is not greater than a predetermined limit of the fast mode scan, the fast mode scan is continued. If the measured x-ray thickness is greater than the predetermined limit of the fast mode scan, the x-rays are turned off, and the operator is given a choice of continuing with the fast mode scan or restarting with a slower mode scan. If the operator selection is to continue, the fast mode scan is continued. If the operator selects restarting, a slower mode scan is commenced.

17 Claims, 7 Drawing Sheets

U.S. PATENT DOCUMENTS

| | | |
|---|---|---|
| 4,358,856 | 11/1982 | Stivender et al. . |
| 4,365,343 | 12/1982 | Grady et al. . |
| 4,403,337 | 9/1983 | Kleinman ................................. 378/95 |
| 4,649,560 | 3/1987 | Grady et al. . |
| 4,715,057 | 12/1987 | Hahn et al. . |
| 4,716,581 | 12/1987 | Barud . |
| 4,788,429 | 11/1988 | Wilson . |
| 4,811,373 | 3/1989 | Stein . |
| 4,829,549 | 5/1989 | Vogel et al. . |
| 4,903,203 | 2/1990 | Yamashita et al. . |
| 5,040,199 | 8/1991 | Stein . |
| 5,132,995 | 7/1992 | Stein . |
| 5,148,455 | 9/1992 | Stein . |
| 5,155,756 | 10/1992 | Pare et al. . |
| 5,165,410 | 11/1992 | Warne et al. . |
| 5,172,695 | 12/1992 | Cann et al. . |
| 5,177,776 | 1/1993 | Ohmori et al. . |
| 5,228,068 | 7/1993 | Mazess . |
| 5,287,546 | 2/1994 | Tesic et al. . |
| 5,291,537 | 3/1994 | Mazess . |
| 5,305,368 | 4/1994 | Bisek et al. . |
| 5,306,306 | 4/1994 | Bisek et al. . |
| 5,432,834 | 7/1995 | Gershman . |

OTHER PUBLICATIONS

The Norland Model 2600 Dichromatic Bone Densitometer Brochure, Norland Corp. (undated).

"DPA gaining strength in bone scanning debate", Diagnostic Imaging, Jun. 1986, pp. 102–108.

Osteotek Brochure, models 200 and 300, Medical & Scientific Enterprises, Inc. (undated).

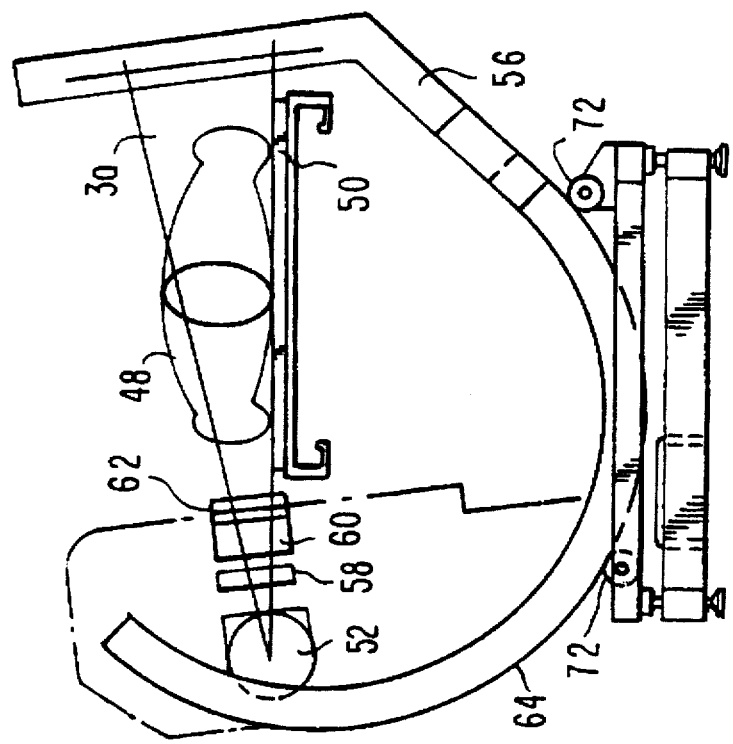
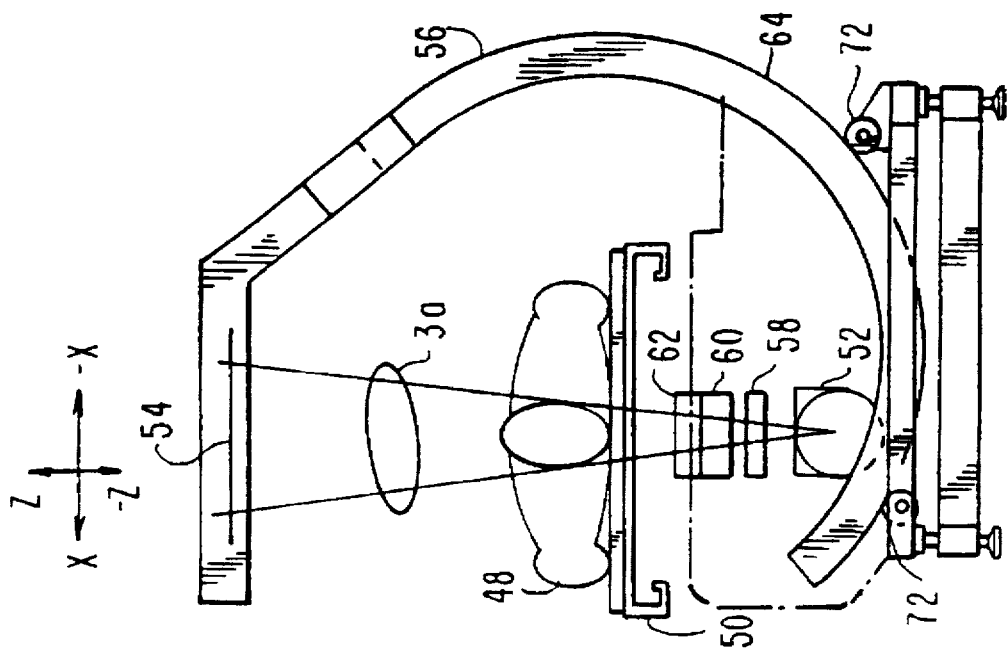
FIG. 3B
FIG. 3A

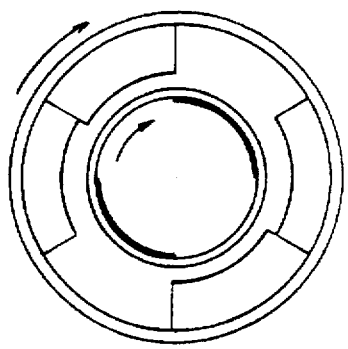
FIG.6C START TISSUE/BRASS
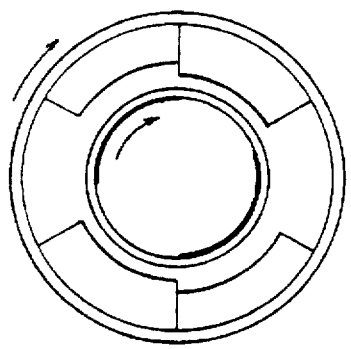
FIG.6F START AIR/AIR
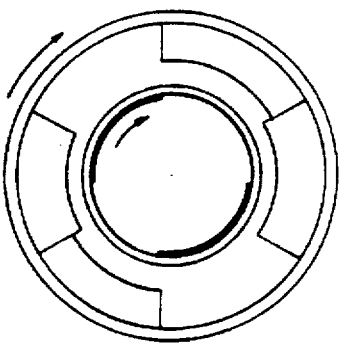
FIG.6B START BONE/AIR
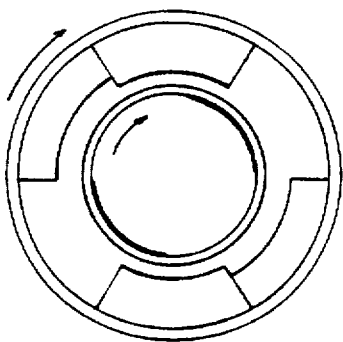
FIG.6E START AIR/BRASS
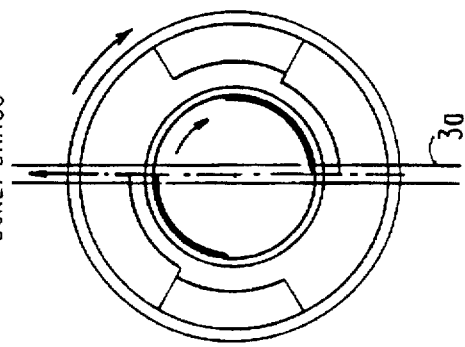
FIG.6A START BONE/BRASS
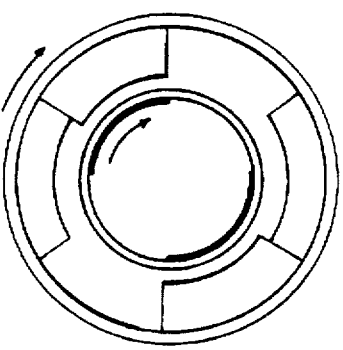
FIG.6D START TISSUE/AIR
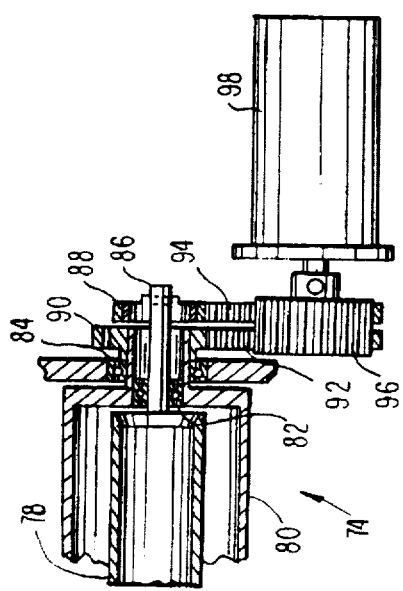
FIG.4
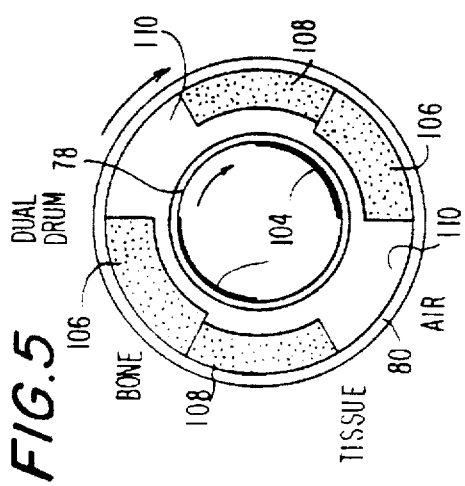
FIG.5

BONE DENSITOMETRY SCANNING SYSTEM AND METHOD FOR SELECTING SCAN PARAMETRIC VALUES USING X-RAY THICKNESS MEASUREMENT

REFERENCE TO RELATED APPLICATIONS

The present invention is a continuation-in-part of application Ser. No. 08/345,069 filed on Nov. 25, 1994, which is a continuation-in-part of Ser. No. 156,287, Nov. 22, 1993, U.S. Pat. No. 5,432,834, both of which are hereby incorporated by reference herein as though fully set forth herein.

FIELD OF THE INVENTION

The present invention relates generally to x-ray based bone densitometry scanning systems and, more particularly, to a method for selecting scan parametric values in the bone densitometry system according to thickness determination.

BACKGROUND OF THE INVENTION

A bone densitometry scanning system can be used to monitor bone conditions associated with diseases such as osteoporosis, and additionally or alternatively, measure non-bone related body content such as body fat and muscle.

Dual energy x-ray absorptiometry (DXA) bone densitometers provide higher and lower energy signals. While single energy techniques provide geometric measurements, DXA systems provide in addition quantitative bone densitometric information. DXA systems also provide digital images with low or no distortion. Furthermore, compared to the single energy technique, DXA systems can have better image contrast in the thoracic region.

Typically, a patient is placed on a table, and a region of interest in the patient is scanned with radiation. The regions of analysis in bone densitometry may be the spine, hip, forearm, and wrist, scanned individually, or the whole body.

Bone densitometry scanning systems provide a choice of predetermined scan modalities which are respective combinations of predetermined specific values for respective scan parameters. Each scan mode presents a corresponding trade off of scan time, spatial resolution and x-ray exposure for the selected region of interest. Operators choose the scan mode that is most appropriate for each patient. Usually, it is desirable to choose the fastest scan mode with the lowest x-ray exposure which will provide satisfactory scan results. However, it is often difficult for the operator to make the determination of the appropriate scan mode.

Thick body region type scans, such as supine lateral, are particularly difficult. When the thickness of the patient exceeds some critical level, the flux of x-ray photons reaching the detectors becomes too low for the scan to provide an acceptable image or precise numerical bone density measurements.

OBJECTS AND SUMMARY OF THE INVENTION

Accordingly, it is an object of this invention to provide a method for assisting an operator of a bone densitometry system to determine the best scan parametric values for a particular patient.

Another object of this invention is to provide a method for determining the best scan parametric values for a particular patient according to a thickness of the patient.

In one example of the invention, after an operator initially selects the default fast scan mode, and the operator starts the scan, the system determines the x-ray equivalent thickness of the patient at the beginning of the scan. If the system determines that the thickness exceeds a preset limit, then the scan is interrupted, and the operator is provided with a choice to restart with a slower scan mode with more exposure. Thus, the operator avoids the situation of having to re-scan a patient after the entire initial scan is found to be unacceptable due to patient thickness.

The system determines patient thickness by comparing the attenuation of the patient in all or some portion of the scan width to known tissue equivalent reference attenuation values. The reference values may include the attenuation for some known thickness that is preferably comparable to the expected patient thickness and the change in attenuation that is expected with the addition or subtraction of some known amount of tissue equivalent thickness.

Because the higher energy signal is less sensitive to small differences in material composition and is less affected by x-ray beam hardening effects, the higher energy signal is more appropriate than the lower energy signal for determining thickness by this method.

BRIEF DESCRIPTION OF THE DRAWINGS

A more complete understanding of the invention may be obtained from the following description when taken in conjunction with the drawings, in which:

FIG. 3A and 3B are end-on views of a patient table and a C-arm of the embodiment of FIG. 2, in the respective positions to perform a PA (posterior-anterior) spine measurement and a lateral spine measurement, respectively.

FIG. 4 is a schematic axial view of a coaxial x-ray modulator of the present invention, shown in partial cross section.

FIG. 5 is a schematic radial view of the x-ray modulator of FIG. 4.

FIGS. 6A–6F show respectively the six rotational combinations of x-ray modulators which may be utilized in the present invention.

DESCRIPTION OF A PREFERRED EMBODIMENT

A method of the present invention is preferably used with the Hologic QDR-4500 bone densitometry scanning system which is a DXA system. The method of the present invention will be described with reference to the accompanying figures which illustrate an implementation with the QDR-4500.

The Scanning System

Figure 1:
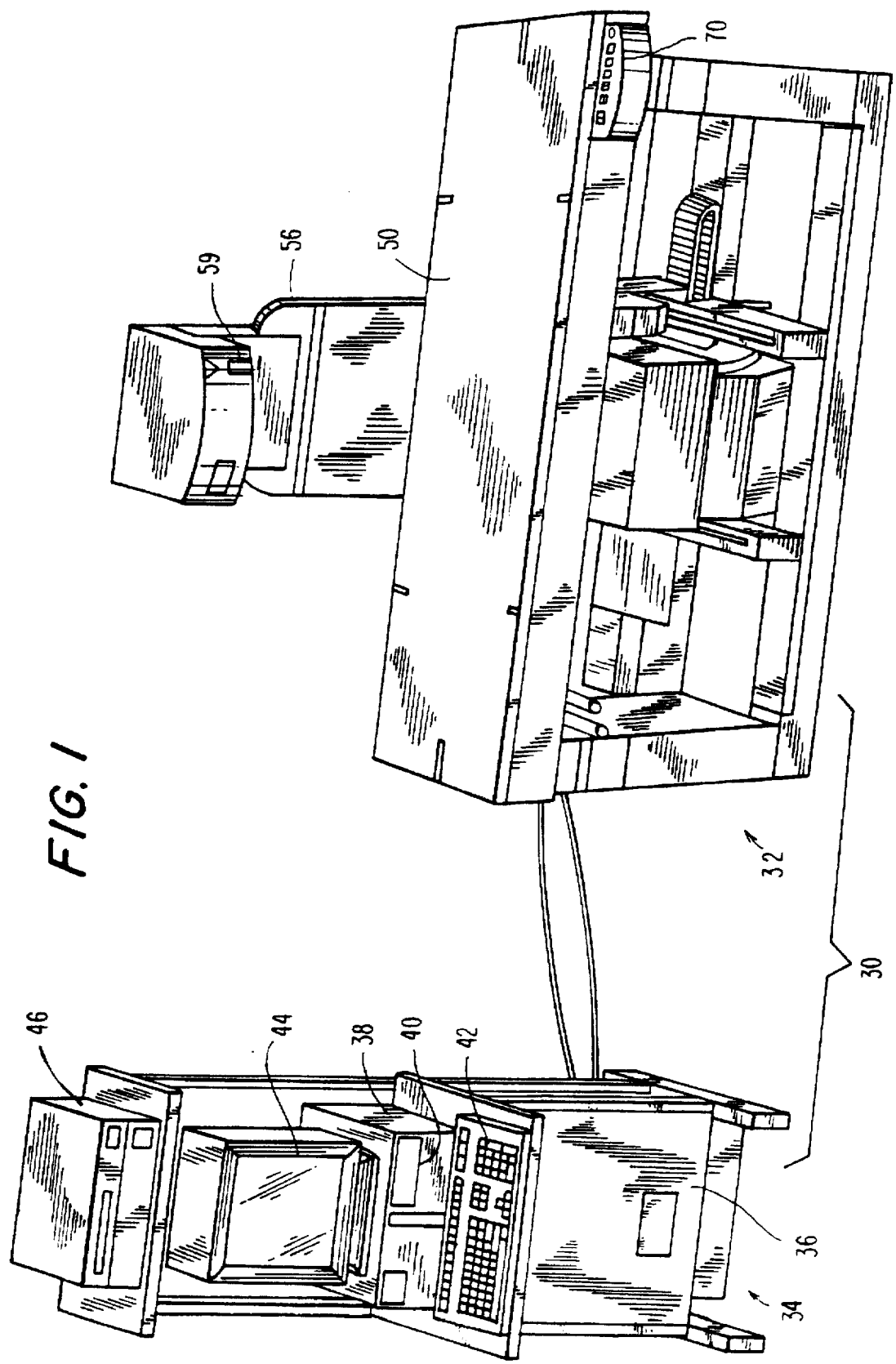
FIG. 1 is a diagrammatic representation of major subsystems of an embodiment of the invention.

Referring to FIG. 1, the bone densitometry scanning system 30 includes an examination table unit 32 comprising a patient table 50 and a C-arm 56 serving as a source-detector support. The scanning system 30 also includes a workstation 34 which controls the examination table unit 32 and C-arm 56 and processes scan data into forms more useful for diagnostic purposes, such as into patient images and reports. The workstation 34 includes a system power supply module 36, a host computer 38 which has a floppy diskette drive recording device 40, an operator console keyboard 42, and a display monitor 44, and can include an optional printer 46.

Referring to FIGS. 3A and 3B, a patient 48 can lie in a supine position on the patient table 50 during scanning. X-rays from a x-ray source 52 located beneath the table 50 pass through the patient 48 and are received by a detector 54 having an array of detector elements located above the patient 48. Each detector element responds to x-rays at respective angular positions within a fan beam of x-rays. Both the x-ray source 52 and the detector 54 are supported on the C-arm 56 which maintains a selected source-to-detector distance and alignment. Therefore, the detector elements are also fixed with respect to the x-ray source 52.

A slit collimator 58 is located between the source 52 and the patient 48. The collimator 58 has one or more selectable slits machined or otherwise formed to allow the passage of x-rays through a slit from the source 52 to the patient 48, and is made of a x-ray opaque material, such as lead or tungsten, of sufficient thickness to substantially block the passage of x-rays through portions of the collimator other than the slits. The x-ray radiation from the x-ray source 52 passes through the slit in the collimator 58 and forms a fan shaped beam of x-rays 3a.

The scanning apparatus also has a x-ray beam modulator 60 which is between the collimator 58 and the patient 48 and can modulate the x-ray beam 3a in a periodic pattern for certain types of diagnostic scanning, including scanning to provide reference and calibration information. There is also an adjustable x-ray beam attenuator 62 for changing the intensity and/or energy spectrum of x-ray beam 3a as desired for different scans and/or other purposes.

Figure 2:
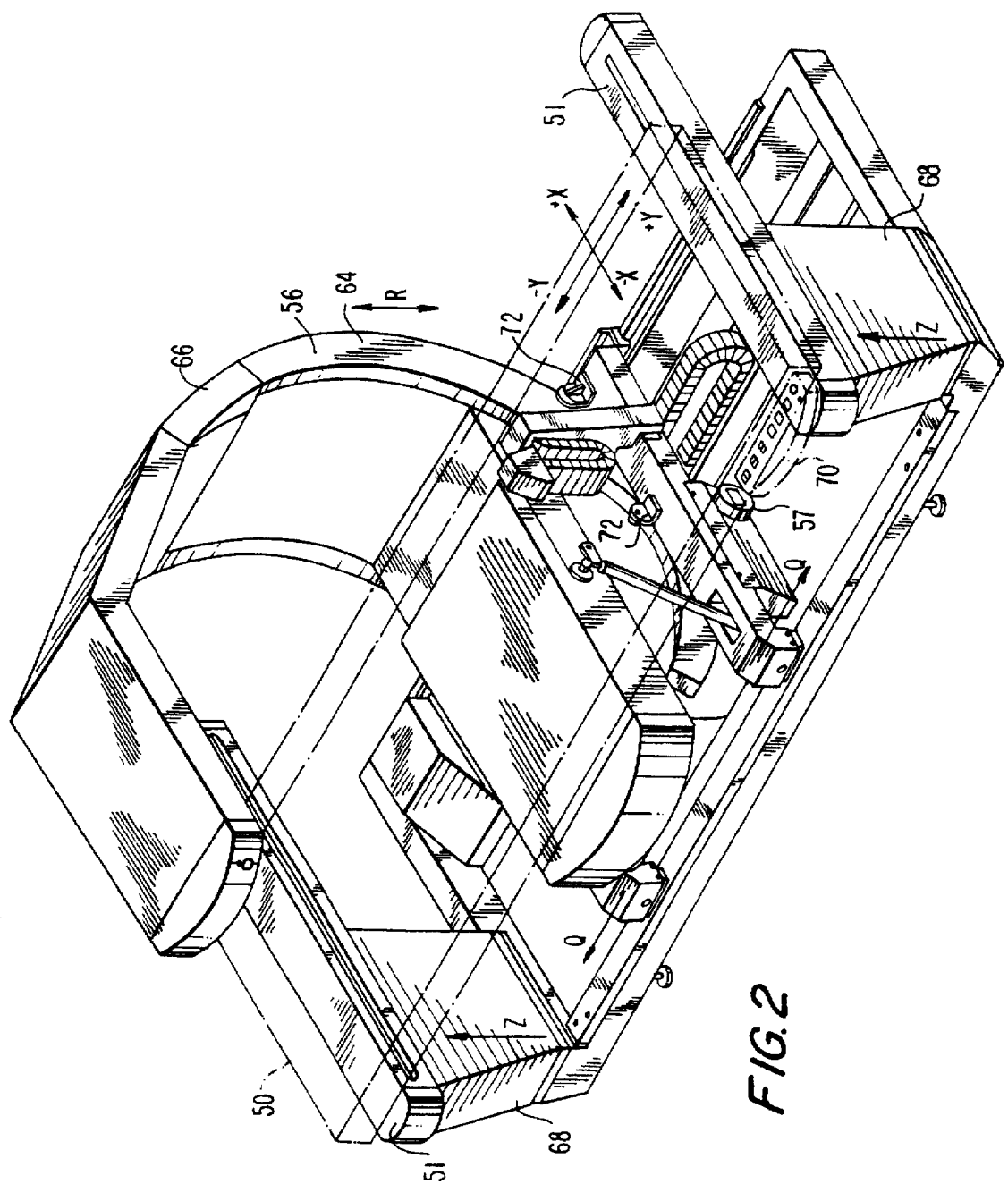
FIG. 2 is a diagrammatic representation of mechanical subsystems of an embodiment of the invention.

As seen in FIGS. 2, 3A and 3B, the C-arm 56 includes a central portion 64 combined with an integrating structure to support the x-ray source 52, the slit collimator 58, the x-ray beam modulator 60 and the x-ray beam attenuator 62. A removable upper arm portion 66 houses the x-ray detector 54, using a bracket interface.

The C-arm 56 rotates essentially within its own volume along rotational path R about a rotational axis extending along the Y-axis which is at the geometric center of portion 64 of the C-arm 56. It is driven rotationally by a mechanism 57 and rides on rollers 72. In addition, the C-arm 56 moves along the Q-axis, along the length of a patient and thus along the patient's spine. The Y-axis and the Q-axis labeled in FIG. 2 extend in the same direction.

The patient support table 50, as seen in FIGS. 2, is translatable along all three axes—the longitudinal (Y axis), the transverse (X axis), and the vertical (Z axis). Each motion is computer controlled and monitored by an absolute encoder feedback system receiving feedback information from an absolute encoder coupled with an idler pulley to provide absolute information respecting any motion of the table 50 in respective directions along a corresponding axis.

The C-arm 56 moves in conjunction with the patient table 50. The geometric/volumetric motion requirements of the C-arm 56 can be seen in FIGS. 3A and 3B. The motions of the table 50 in the transverse and vertical directions help the C-arm 56 clear the table 50 when rotating between the two illustrated positions of the C-arm 56 which correspond to a PA scan and a lateral scan of the spine, respectively.

As carried on the C-arm 56, the x-ray source 52 and the detector 54 have a 2-axis motion with respect to the patient 48 to carry out scans. Motion in the longitudinal Y (or Q) direction moves them along the patient axis as defined by the spine. A second motion, along the R rotational path, rotates the x-ray source 52 and the detector 54 around the patient, the center of rotation being at a point C which is determined by the C-arm 56 and the method of rotation employed.

To perform a scan, a series of scan lines of data are acquired. The C-arm 56 and the patient table 50 are moved in a coordinated manner, as described hereinabove, to appropriate positions corresponding to the desired scan. FIG. 3A illustrates such positioning for a PA scan of the spine. Thereafter, the C-arm 56, carrying the x-ray source 52 and the detector 54, moves along the Q-axis along a portion of the length of the patient 48. This motion moves the detector 54 and the x-ray source 52 to form a succession of spatially overlapping scan lines adding up to a scanned rectangular area. The signals produced by the detector elements in detector 54 in response to x-rays impinging thereon at successive scan lines are digitized by an analog to digital (A/D) converter and are stored, for example on disk. The host computer 38 processes the signals from the A/D converter into density representations, and/or images, and/or reports of measured and/or calculated parameters, using principles disclosed in the material referenced in the background section of this disclosure.

FIG. 3B shows the positioning for a lateral scan of the spine. To attain this position, table 50 is moved along the X-axis and the Z-axis appropriately, while C-arm 56 is rotated about an axis passing through point C and parallel with the Y-axis until the desired lateral position is reached. Thereafter, while the C-arm 56 moves along the Q-axis along a portion of the length of the patient 48, a lateral scan is acquired for that portion of the spine.

Figure 7:
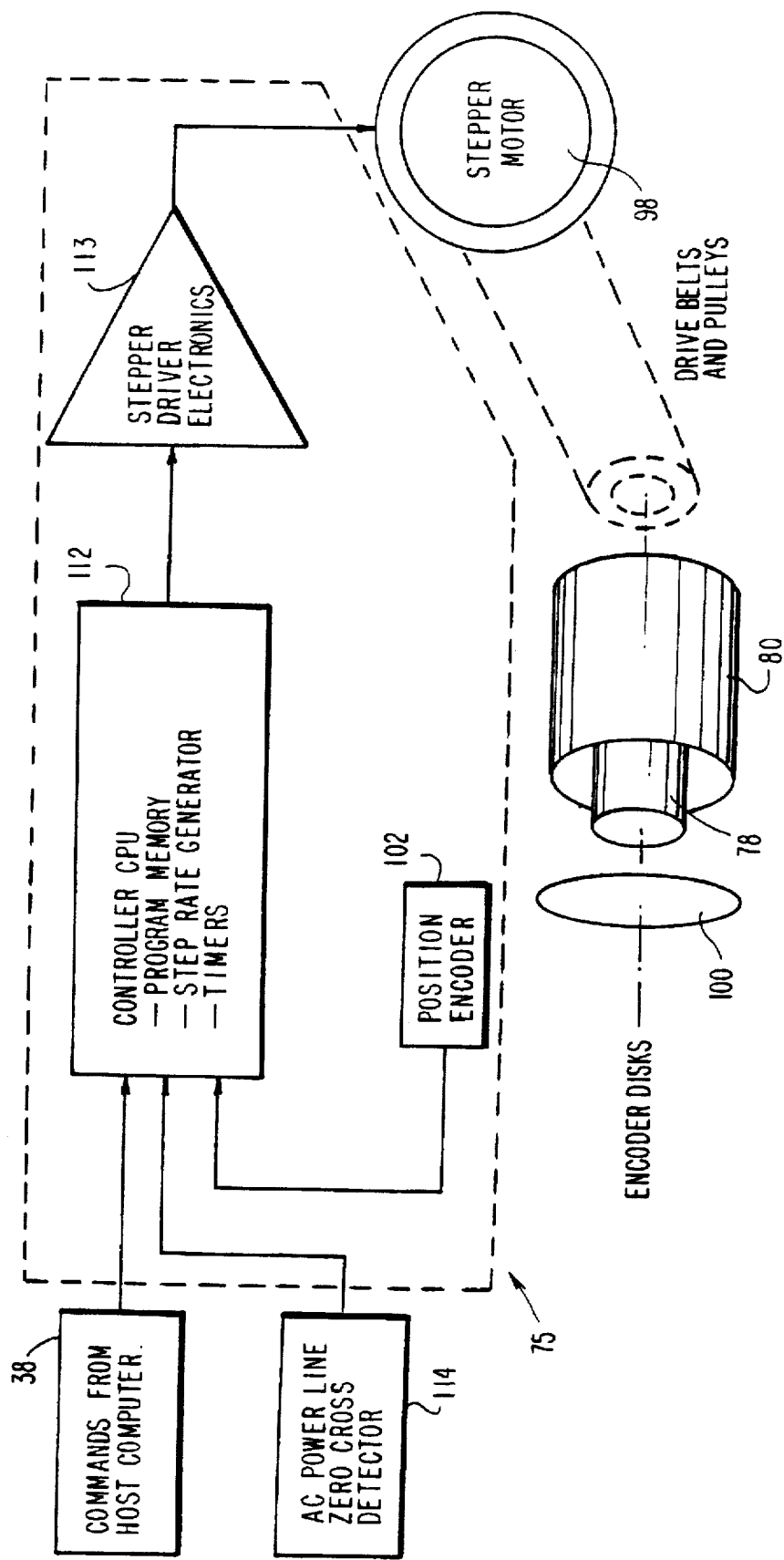
FIG. 7 is a controller block diagram for the x-ray modulator of FIG. 4.

The reference and modulation system 60 comprises a drum assembly 74 seen in FIGS. 4 and 5, and a control system 75 seen in FIG. 7.

Referring to FIGS. 4 and 5, the drum assembly 74 has a pair of nested, preferably coaxial, hollow inner and outer cylinders 78, 80, respectively, on separate bearing sets 82, 84, respectively, which allow the cylinders to rotate freely relative to each other. Shaft 86 for the inner cylinder 78 does not extend into the cylinder 78, so that its center remains hollow. Respective toothed pulleys 88, 90 are mounted on respective ends of each cylinders 78, 80, and they are connected via respective timing belts 92, 94 to a single drive pulley 96 mounted on modulator drive motor 98.

As seen in FIG. 7, encoder disks 100 and position encoders 102 (only one is shown for conciseness) for measuring the angular positions of respective cylinders 78, 80 are mounted at the opposite end of the drive system. Both the position encoders 102 and the motor 98 are coupled to the control system 75.

As seen in FIG. 5, the inner cylinder 78 is divided into four 90 degree sections, with two brass strips 104 located 180 degrees across from each other. As the inner cylinder 78 rotates, a sequence of brass, air, brass, air, etc., at 50% duty cycle is generated. The outer cylinder 80 is divided into six, 60 degree segments. At two opposing segment locations are mounted bone simulating materials 106; another pair of opposing segments have tissue simulating material 108, and the last two locations are left empty and referred to as air segments 110. Rotation of the outer cylinder 80 therefore creates the periodic sequence of bone, tissue, air, bone tissue, air, etc. As seen in FIGS. 6A–6F, when both cylinders 78, 80 rotate in accordance with the previously defined cylinder rotational ratios, the x-ray beam 3a passing through the center of rotation would be modified by the following sequence of attenuation materials: bone+brass; bone+air; tissue+brass; tissue+air; air+brass; air+air; followed by a repeat of the same pattern for the second half of the outer cylinder.

The modulator control system 75 is illustrated in FIG. 7 and comprises a circuit board having a microcomputer CPU 112 and interface circuitry. Control programs for operating such as the microcomputer 112 are stored in electronic memory, an EPROM memory device. Inputs to the system are commands from the host control computer 38, AC power frequency timing information from zero crossing detector 114 and signals from the positional encoders 102 of the drum assembly 74. The outputs of the control system 75 are motor step pulses to stepper driver electronics 113 and system status information to host control computer 38.

In operation, the rotational axis of modulator drum assembly 74 is positioned along the long axis of the x-ray fan beam 3a through mechanical alignment. As x-rays within the fan beam 3a travel from the source 52 toward the detector 54, they pass first through one wall of the outer cylinder 80, then through the material mounted on the inside of the outer cylinder 80, then through the wall of the inner cylinder 78, then through the material mounted on the inside of the inner cylinder 78, and so on, until the beam 3a exits the other wall of the outer cylinder 80, as shown in FIGS. 8A–8F. When the two cylinders 78, 80 are stationary, the x-ray beam 3a is modified by the composite stack of materials present in its path. When cylinders 78, 80 are rotating, a sequence of different material combinations are inserted into the path of the x-ray beam 3a in a periodic, repetitive fashion, as determined by the controller CPU 112 directing the drive motor system. The sequence and/or timing of the material combinations which attenuate the beam 3a can be modified by changing controller programming.

Figure 8:
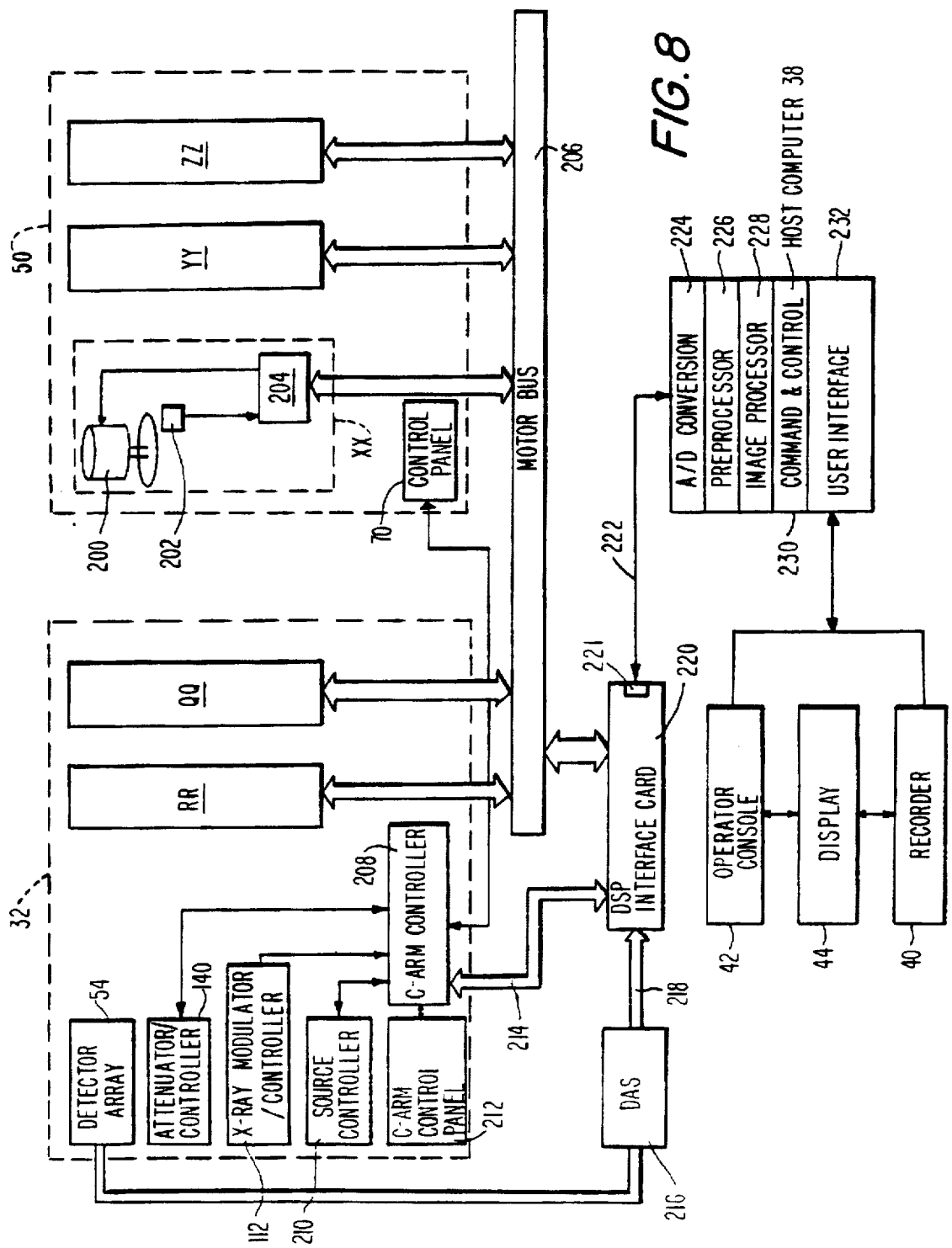
FIG. 8 is a block diagram illustrating electrical and electronic systems of an embodiment of the invention.

FIG. 8 illustrates, in block diagram form, scanner electrical and electronic control systems. The examination table unit 32 includes the structure illustrated in FIGS. 1 and 2, as well as motors for driving the patient support table 50 and the C-arm 56, respectively, and to operate the attenuator 62 and the modulator 60. Each of the motors has a local controller with motor driver electronics and position encoder, similar to those used in the x-ray modulator system shown in FIG. 7. For the sake of conciseness, each of those local elements is not repeated in this figure.

In FIG. 8, drive system XX which causes X direction translation of the patient table 50 is shown as including a motor 200, a motor position encoder 202 and local X motion controller/motor driver electronics 204. For the sake of brevity, similar structure for the Y direction translation of the patient table is shown as block YY, and Z direction patient table translation as block ZZ. Block RR depicts a rotation drive system for the C-arm 56, with local controller, and block QQ denotes the translation of the C-arm 56 in the Q direction. The respective local controllers for drive systems XX, YY, ZZ, QQ and RR communicate over motor bus 206.

As further shown in FIG. 8, the C-arm 56 has a C-arm local controller 208, which communicates with x-ray source controller 210, the CPU 112 of the x-ray modulator controller 75, the x-ray attenuator controller 140 and control panels 212, 70 located in the C-arm 56 and patient table 50, respectively. The C-arm controller 208 communicates via C-arm controller bus 214.

The detector array 54 supplies x-ray measurements to data acquisition system (DAS) 216, where the measurements are collected and can be preliminarily processed. The DAS 216 outputs its collected and processed x-ray measurements from the individual elements of the detector array 54 via DAS bus 218.

Digital Signal Processor (DSP) 220 is coupled to each of the motor bus 206, the C-arm controller bus 214, and the DAS bus 218, and functions as a communications exchange for remote controllers with the host computer system 38. The DSP 220 includes an interface 221 for communication with the host computer via a communications line 222.

The DSP 220 is responsible for real-time processing, such as motion control over the table 50 and the C-arm 56. Scan data from the DAS 216 and its corresponding position data obtained from the scanning system patient table and C-arm position encoders (e.g., 202) can be stored in DSP data buffers (not shown).

In order to perform scan data processing, scan data from the DAS 216 is forwarded to the host computer 38, which is programmed to perform A/D conversion 224 and preliminary data preprocessing 226. The output of the preliminary data preprocessing functions 226 is supplied to an image processing program 228, which performs various calculations and forms an image and, additionally, blends the data from successive scans to form whole-body images by using among other things, the patient table and C-arm positional encoder data. Data and images from the image processing program 228 are supplied to a console 42, display 44 and a recorder such as the floppy disk drive 40 and/or the printer 46.

The host computer is also programmed to provide command and control 230 to the various controllers, and to provide user interface 232.

Selecting the Appropriate Scan Parametric Values

The bone densitometer 30 provides both "Fast Array" and "Array" mode supine lateral scans. The Array scan mode has one-half the scan speed and therefore twice the x-ray exposure of the Fast Array mode. In this preferred embodiment, the Fast Array mode scan can be applied to a limit of 13.5 inches of patient thickness.

Figure 9:
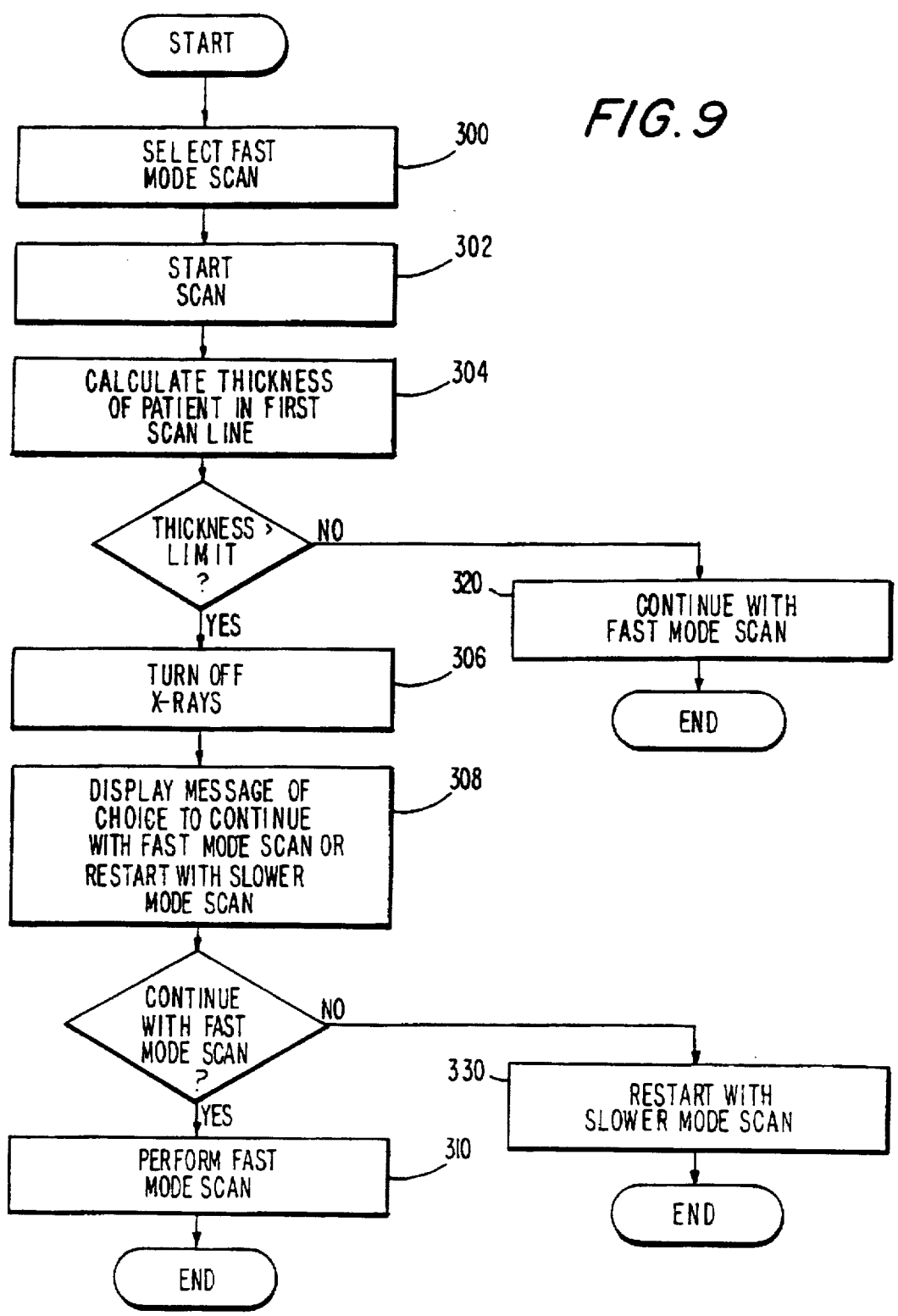
FIG. 9 is a flow chart showing a method for determining the best scan parametric values according to a x-ray thickness of a particular patient according to the present invention.

The user interface 232 assists the operator to determine the best scan parametric values for the patient 48. Referring to FIG. 9, when the operator sets up the system 30 for a supine lateral type scan, the user interface 232 recommends to the operator via the display 44 a Fast Array mode scan as the default. While the operator can select another mode, typically the operator will initially select the Fast Array scan mode and start the scan. When the scan begins, the system 30 determines the x-ray thickness of the patient 48 in the first scan line. "X-ray thickness" refers to the way a material affects x-rays passing therethrough. Thus, a 1 cm thick piece of bone would typically have a greater x-ray thickness than a 1 cm thick layer of soft tissue because the same thickness of material would attenuate the x-rays to a greater degree because of its greater density.

The system 30 determines patient thickness by comparing the attenuation of the patient in all or some portion of the scan width to known tissue equivalent reference attenuation values. The reference values may include the attenuation for a predetermined thickness that is preferably comparable to the expected patient thickness, and may also include the change in attenuation which is expected with the addition or subtraction of a predetermined amount of tissue equivalent thickness.

As stated hereinabove, the system 30 is a DXA system which employs a three segment reference filtration system 60. Accordingly, the scan data is in the form of six phases that are designated as HI_AIR, LO_AIR, HI_TISSUE, LO_TISSUE, HI_BONE and LO_BONE, which are defined as follows:

HI_AIR—signal from the higher energy x-rays unfiltered by the filtration system 60;

LO_AIR—signal from the lower energy beam unfiltered by the filtration system 60;

HI_TISSUE—signal from the higher energy x-rays filtered through approximately 0.5 inches of soft tissue equivalent material;

LO_TISSUE—signal from the lower energy beam filtered through approximately 0.5 inches of soft tissue equivalent material;

HI_BONE—signal from the higher energy x-rays filtered through bone equivalent material with a density of approximately 1 g/cm$^2$; and LO_BONE—signal from the lower energy x-rays filtered through bone equivalent material with a density of approximately 1 g/cm$^2$.

During calibration the system 30 scans a calibration phantom (not shown) that is approximately 7 inches thick. A variety of measurements from the calibration using the phantom are recorded on the system. The thickness calculation uses the following measurements and stored values:

$T_O$—x-ray thickness of the calibration phantom;
HiA—HI_AIR attenuation of the calibration phantom;
HiT—HI_TISSUE attenuation of the calibration phantom;
$\Delta T$—thickness of the tissue equivalent filter material; and
AvgPatHiAir—mean value of HI_AIR attenuation measured in the patient during the first scan line.

The system 30 uses the following equation for calculating patient thickness is:

$$\text{Patient thickness} = T_O + \Delta T^*(\text{AvgPatHiAir} - \text{HiA})/(\text{HiT} - \text{HiA}).$$

In order to restrict determination of the patient thickness to the area near the bone on supine lateral scans, AvgPatHiAir is calculated using data only from the central three quarters of the scan width.

Because the higher energy signal is less sensitive to small differences in material composition and is less affected by x-ray beam hardening effects, the higher energy signal is preferred over the lower energy signal for calculating thickness by this method.

While in the preferred embodiment the values HiA and HiT are obtained from measurements of the higher energy x-rays in a dual energy system, an alternative embodiment can use the lower energy x-rays in place of the higher energy x-rays. Thus, the values HiA and HiT referred to in the claims can derive either from the higher energy x-rays or the lower energy x-rays or a combination, such as a linear combination, of a signal derived from the higher energy x-rays and a signal derived from the lower energy x-rays, unless a claim specifically states otherwise.

If the determined thickness exceeds the limit for a Fast Array mode scan, then the x-rays are turned off and a message is displayed that provides the operator with a choice of continuing with the Fast Array mode scan or restarting with the slower Array mode scan. By selecting the Array mode scan, the operator can avoid having to re-scan a patient after the initial scan is found to be unacceptable due to patient thickness.

However, the operator may nevertheless choose to continue with the Fast Array mode because specific instructions have been issued to the operator or the operator is required to follow a particular research protocol. In the case that the operator chooses to continue with the Fast Array mode scan in spite of the recommendation, no further thickness checking is performed.

Having described a preferred embodiment of the invention with reference to the accompanying drawings, it is to be understood that the invention is not limited to that precise embodiment and that various changes and modifications thereof could be effected by one skilled in the art without departing from the spirit or scope of the novel concepts of the invention, as defined in the appended claims. For example, while the specific algorithm used to determine patient thickness is embodied as an implementation for Hologic QDR-4500 bone densitometry system, the algorithm can be readily adapted to other bone DXA systems by persons skilled in the art.

What is claimed is:

1. A method of selecting a best scan mode for a x-ray bone densitometry scanning system according to a x-ray thickness of a patient, comprising the steps of:
   (a) selecting a fast mode as a default;
   (b) starting a fast mode scan;
   (c) obtaining a measured thickness signal related to the x-ray thickness of the patient at an initial portion of the scan;
   (d) continuing the fast mode scan if the measured thickness signal conforms to a predetermined limit of the fast mode scan; and
   (e) restarting with a slower mode scan if the measured thickness signal does not conform to the predetermined limit of the fast mode scan.

2. The method according to claim 1 wherein the step (e) includes:
   turning off x-rays;
   displaying on a display of the x-ray bone densitometry scanning system a message of the available alternatives of continuing with the fast mode scan or restarting with a slower mode scan;
   reading an operator selection via a console of the x-ray bone densitometry scanning system;
   continuing the fast mode scan if the operator selection is to continue with the fast mode scan; and
   restarting with a slower mode scan if the operator selection is to restart with the slower mode scan.

3. The method according to claim 1 wherein the x-ray bone densitometry scanning system is a DXA system, and the step (c) includes:
   performing a calibration of the system by scanning a calibration phantom having a x-ray thickness $T_O$;
   receiving x-rays through the calibration phantom to derive a first signal;
   determining an attenuation value HiA of the first signal;
   receiving through the calibration phantom x-rays filtered through a predetermined thickness $\Delta T$ of soft tissue equivalent material to derive a second signal;
   determining an attenuation value HiT of the second signal;
   receiving through the patient x-rays via a plurality of x-ray detectors to derive a respective plurality of signals during at least one scan line at an initial portion of the scan;
   determining a plurality of attenuation values for the respective plurality of signals received via the respective plurality of x-ray detectors;
   calculating a mean value AvgPatHiAir of the plurality of attenuation values for the respective plurality of signals; and
   calculating the thickness of the patient using the following formula, $$\text{patient thickness} = T_O + \Delta T^*(\text{AvgPatHiAir} - \text{HiA})/(\text{HiT} - \text{HiA}).$$

4. The method according to claim 3 wherein the first signal, the second signal and the plurality of signals received via the respective plurality of x-ray detectors are each derived from receiving higher energy x-rays in the DXA system.

5. The method according to claim 3 wherein the first signal, the second signal, and the plurality of signals received via the respective plurality of x-ray detectors are each derived from a linear combination of higher energy x-rays and lower energy x-rays in the DXA system.

6. A method of selecting a best scan mode for a x-ray bone densitometry scanning system according to a x-ray thickness of a patient, comprising the steps of:

(a) selecting a fast mode as a default;

(b) starting a fast mode scan;

(c) determining a measured thickness signal related to the x-ray thickness of the patient at an initial portion of the scan;

(d) continuing the fast mode scan if the measured x-ray thickness signal conforms to a predetermined limit of the fast mode scan; else (e) turning off x-rays;

(f) displaying on a display of the x-ray bone densitometry scanning system a message of the available alternatives of continuing with the fast mode scan or restarting with a slower mode scan;

(g) reading an operator selection via a console of the x-ray bone densitometry scanning system;

(h) continuing the fast mode scan if the operator selection is to continue with the fast mode scan; and (i) restarting with a slower mode scan if the operator selection is to restart with the slower mode scan.

7. The method according to claim 4 wherein the x-ray bone densitometry scanning system is a DXA system, and the step (c) includes:

performing a calibration of the system by scanning a calibration phantom having a x-ray thickness $T_O$;

receiving x-rays through the calibration phantom to derive a first signal;

determining an attenuation value HiA of the first signal;

receiving through the calibration phantom x-rays filtered through a predetermined thickness $\Delta T$ of soft tissue equivalent material to derive a second signal;

determining an attenuation value HiT of the second signal;

receiving through the patient x-rays via a plurality of x-ray detectors to derive a respective plurality of signals during at least one scan line at an initial portion of the scan;

determining a plurality of attenuation values for the respective plurality of signals received via the respective plurality of x-ray detectors;

calculating a mean value AvgPatHiAir of the plurality of attenuation values for the respective plurality of signals; and calculating the thickness of the patient using the following formula, patient thickness=$T_O$ +$\Delta T$*(AvgPatHiAir−HiA)/(HiT−HiA).

8. The method according to claim 7 wherein the first signal, the second signal and the plurality of signals received via the respective plurality of x-ray detectors are each derived from receiving higher energy x-rays in the DXA system.

9. The method according to claim 7 wherein the first signal, the second signal, and the plurality of signals received via the respective plurality of x-ray detectors are each derived from a linear combination of higher energy x-rays and lower energy x-rays in the DXA system.

10. The method according to claim 6 wherein a scan speed of the fast mode scan is double a speed of the slower mode scan.

11. The method according to claim 6 wherein the predetermined limit of the fast mode scan is 13.5 inches.

12. The method according to claim 7 wherein the thickness of the calibration phantom is approximately 7 inches.

13. The method according to claim 7 wherein the mean value AvgPatHiAir is calculated using only attenuation values of ones of the plurality of signals received via the respective plurality of detectors which are from a central three quarters of a scan width.

14. A method of selecting scan parametric values of a x-ray bone densitometry scanning system for a particular patient according to a x-ray thickness of the patient, comprising the steps of:

(a) selecting a plurality of scan parametric values of a fast mode as a default;

(b) starting a fast mode scan having the plurality of selected scan parametric values;

(c) determining a measured thickness signal related to the x-ray thickness of the patient at an initial portion of the scan;

(d) continuing the fast mode scan if the measured x-ray thickness signal conforms to a predetermined limit of the fast mode scan; else (e) turning off x-rays;

(f) displaying on a display of the x-ray bone densitometry scanning system a message of the available alternatives of continuing with the fast mode scan or restarting with a slower mode scan;

(g) reading an operator selection via a console of the x-ray bone densitometry scanning system;

(h) continuing the fast mode scan if the operator selection is to continue with the fast mode scan; and (i) restarting with a slower mode scan if the operator selection is to restart with the slower mode scan.

15. The method according to claim 10 wherein the x-ray bone densitometry scanning system is a DXA system, and the step (c) includes:

performing a calibration of the system by scanning a calibration phantom having a x-ray thickness $T_O$;

receiving x-rays through the calibration phantom to derive a first signal;

determining an attenuation value HiA of the first signal;

receiving through the calibration phantom x-rays filtered through a predetermined thickness $\Delta T$ of soft tissue equivalent material to derive a second signal;

determining an attenuation value HiT of the second signal;

receiving through the patient x-rays via a plurality of x-ray detectors to derive a respective plurality of signals during at least one scan line at an initial portion of the scan;

determining a plurality of attenuation values for the respective plurality of signals received via the respective plurality of x-ray detectors;

calculating a mean value AvgPatHiAir of the plurality of attenuation values for the respective plurality of signals; and calculating the thickness of the patient using the following formula, patient thickness=$T_O + \Delta T*(\text{AvgPatHiAir}-\text{HiA})/(\text{HiT}-\text{HiA})$.

16. The method according to claim 15 wherein the first signal, the second signal and the plurality of signals received via the respective plurality of x-ray detectors are each derived from receiving higher energy x-rays in the DXA system.

17. The method according to claim 15 wherein the first signal, the second signal, and the plurality of signals received via the respective plurality of x-ray detectors are each derived from a linear combination of higher energy x-rays and lower energy x-rays in the DXA system.

* * * * *